(12) United States Patent
Zhu

(10) Patent No.: US 11,916,334 B1
(45) Date of Patent: Feb. 27, 2024

(54) COMBINED TYPE HAND WARMER

(71) Applicant: Guangdong Aoyun Technology Co., Ltd., Guangdong (CN)

(72) Inventor: Xueping Zhu, Guangdong (CN)

( * ) Notice: Subject to any disclaimer, the term of this patent is extended or adjusted under 35 U.S.C. 154(b) by 0 days.

(21) Appl. No.: 17/967,744

(22) Filed: Oct. 17, 2022

(30) Foreign Application Priority Data

Aug. 5, 2022 (CN) .......................... 202222063218.4

(51) Int. Cl.
*A61F 7/00* (2006.01)
*H05B 3/06* (2006.01)
*H01R 13/627* (2006.01)
*H01R 24/00* (2011.01)

(52) U.S. Cl.
CPC ......... *H01R 13/6278* (2013.01); *A61F 7/007* (2013.01); *H01R 24/00* (2013.01); *H05B 3/06* (2013.01); *A61F 2007/0036* (2013.01); *A61F 2007/0087* (2013.01); *A61H 2205/065* (2013.01)

(58) Field of Classification Search
None
See application file for complete search history.

(56) References Cited

U.S. PATENT DOCUMENTS

| | | | | |
|---|---|---|---|---|
| 5,614,292 A * | 3/1997 | Saylor | ...................... | H05B 3/36 428/209 |
| 6,423,951 B1 * | 7/2002 | Elsasser | ................... | H05B 3/06 219/544 |
| 2004/0109681 A1 * | 6/2004 | Yue | ........................ | H05B 3/283 392/435 |
| 2011/0253694 A1 * | 10/2011 | Consiglio | ............. | F24D 13/024 219/213 |
| 2016/0014847 A1 * | 1/2016 | Jeong | ..................... | H05B 3/286 219/541 |
| 2017/0352928 A1 * | 12/2017 | Lingenfelter | ....... | H01M 50/247 |
| 2019/0090313 A1 * | 3/2019 | Jones, Sr. | ................ | H05B 3/22 |
| 2020/0103124 A1 * | 4/2020 | Nyström | ........... | E04F 15/02038 |
| 2021/0079613 A1 * | 3/2021 | Jones, Sr. | ............... | E01H 5/108 |

(Continued)

FOREIGN PATENT DOCUMENTS

| | | | |
|---|---|---|---|
| CN | 210320254 U | * | 4/2020 |
| CN | 213285543 U | * | 5/2021 |
| CN | 216121866 U | * | 3/2022 |

(Continued)

OTHER PUBLICATIONS

CN210320254U, Apr. 2020, Liu, Bib data sheet (Year: 0420).*

(Continued)

*Primary Examiner* — Joseph M. Pelham

(57) ABSTRACT

The present disclosure provides a combined type hand warmer, including a first hand warmer unit and a second hand warmer unit; a first connection part is arranged on the first hand warmer unit, and a second connection part is arranged on the second hand warmer unit; the first connection part is detachably connected to the second connection part such that the first hand warmer unit and the second hand warmer unit are combined into a whole; and when a user needs to warm two hands/multiple body parts, the first hand warmer unit can be separated from the second hand warmer unit, and the first hand warmer unit and the second hand warmer unit can be respectively used for warming the two hands/multiple body parts.

8 Claims, 5 Drawing Sheets

(56) References Cited

U.S. PATENT DOCUMENTS

2023/0086468 A1* 3/2023 Lanzl .................. F25D 21/04
2023/0089289 A1* 3/2023 Schneider ............ G01V 3/088
　　　　　　　　　　　　　　　　　　　　　　219/204

FOREIGN PATENT DOCUMENTS

KR　　　101989309 B1 *　6/2019
SK　　　　1782020 U1 *　3/2021

OTHER PUBLICATIONS

KR-101989309-B1, Jun. 2019, Bib data sheet, Kim et al (Year: 2019).*
R-101989309-B1, Jun. 2019, partial tranls., Kim et al (Year: 2019).*

* cited by examiner

COMBINED TYPE HAND WARMER

CROSS-REFERENCE TO RELATED APPLICATIONS

The application claims priority of Chinese patent application CN2022220632184, filed on 2022 Aug. 5, which is incorporated herein by reference in its entireties.

TECHNICAL FIELD

The present disclosure relates to the field of hand warmers, in particular, to a combined type hand warmer.

BACKGROUND

Existing hand warmers on the market, whether they are double-sided or single-sided, can usually only be used for warming one hand/one body part, and it is difficult to warm both hands/multiple body parts at the same time. Particularly, when a user has to do different actions with two hands or when a plurality of parts of the user need to be warmed, the current hand warmer can hardly meet the need of the user. Therefore, there is an urgent need to provide a hand warmer that can be used for warming two hands/multiple body parts at the same time and is easy for users to carry.

SUMMARY

In order to overcome the defects of the prior art, the present disclosure provides a combined type hand warmer, which can be used for warming two hands/multiple body parts and is convenient for a user to carry.

The present disclosure adopts the following technical solution: a combined type hand warmer including a first hand warmer unit and a second hand warmer unit; a first connection part is arranged on the first hand warmer unit, and a second connection part is arranged on the second hand warmer unit; and the first connection part is detachably connected to the second connection part such that the first hand warmer unit and the second hand warmer unit are combined into a whole.

Further, the first connection part includes a first buckle, and the second connection part includes a first buckle slot; and the first buckle is detachably plugged to the first buckle slot.

Further, the first connection part further includes a second buckle slot, and the second connection part further includes a second buckle; and when the first buckle is detachably plugged to the first buckle slot, the second buckle is detachably plugged to the second buckle slot.

Further, the first connection part further includes a first positioning pillar, and the second connection part further includes a first positioning hole; and when the first positioning pillar is located in the first positioning hole, the first buckle is detachably plugged to the first buckle slot, and the second buckle is detachably plugged to the second buckle slot.

Further, the first connection part further includes a second positioning hole, and the second connection part further includes a second positioning pillar; and when the first positioning pillar is located in the first positioning hole, and the second positioning pillar is located in the second positioning hole, the first buckle is detachably plugged to the first buckle slot, and the second buckle is detachably plugged to the second buckle slot.

Further, the first connection part further includes a first guide slot; the first positioning pillar is located on an upper side of the first guide slot, and the second positioning hole is located on a lower side of the first guide slot; the second connection part further includes a second guide slot; the first positioning hole is located on an upper side of the second guide slot, and the second positioning pillar is located on a lower side of the second guide slot; and when the first positioning pillar slides into the first positioning hole along the second guide slot, and the second positioning pillar slides into the second positioning hole along the first guide slot, the first buckle is detachably plugged to the first buckle slot, and the second buckle is detachably plugged to the second buckle slot.

Further, the first buckle is arranged on one side of the first hand warmer unit, and the second buckle slot is symmetrically arranged on the other side of the first hand warmer unit; and the second buckle is arranged on one side of the second hand warmer unit, and the first buckle slot is symmetrically arranged on the other side of the second hand warmer unit.

Further, a first charging port is further arranged on the first hand warmer unit; the first charging port is used for charging the first hand warmer unit; a second charging port is further arranged on the second hand warmer unit; and the second charging port is used for charging the second hand warmer unit.

Further, a first power indicator is further arranged on the first hand warmer unit; the first power indicator is used for displaying the battery power of the first hand warmer unit; a second power indicator is further arranged on the second hand warmer unit; and the second power indicator is used for displaying the battery power of the second hand warmer unit.

Further, a first on/off button is further arranged on the first hand warmer unit; the first on/off button is used for controlling the first hand warmer unit to be turned on/off; a second on/off button is further arranged on the second hand warmer unit; and the second on/off button is used for controlling the second hand warmer unit to be turned on/off.

The present disclosure has the beneficial effects: the combined type hand warmer includes the first hand warmer unit and the second hand warmer unit; the first connection part is arranged on the first hand warmer unit, and the second connection part is arranged on the second hand warmer unit; and the first connection part is detachably connected to the second connection part such that the first hand warmer unit and the second hand warmer unit are combined into a whole. Therefore, when a user needs to warm two hands/multiple body parts, the first hand warmer unit can be separated from the second hand warmer unit, and the first hand warmer unit and the second hand warmer unit can be respectively used for warming the two hands/multiple body parts. When the user only needs to warm one hand/one body part, the first connection part can be connected to the second connection part to combine the first hand warmer unit with the second hand warmer unit into a whole, so as to enlarge a warming area of the hand warmer for one hand/one body part and enhance the warming effect. Furthermore, when the user needs to carry or store the hand warmer, the user selects, according to an actual situation, either to separately carry or store the first hand warmer and the second hand warmer, or to carry or store the first hand warmer and the second hand warmer as a whole, so as to satisfy a plurality of use scenarios of the user and greatly improve the experience of the user.

BRIEF DESCRIPTION OF THE DRAWINGS

Implementations of the present disclosure will now be described, by way of embodiment, with reference to the attached figures. It should be understood, the drawings are shown for illustrative purpose only, for ordinary person skilled in the art, other drawings obtained from these drawings without paying creative labor by an ordinary person skilled in the art should be within scope of the present disclosure.

FIG. 1 is a schematic diagram of an overall structure of the present disclosure.

DETAILED DESCRIPTION OF THE EMBODIMENTS

Figure 1:
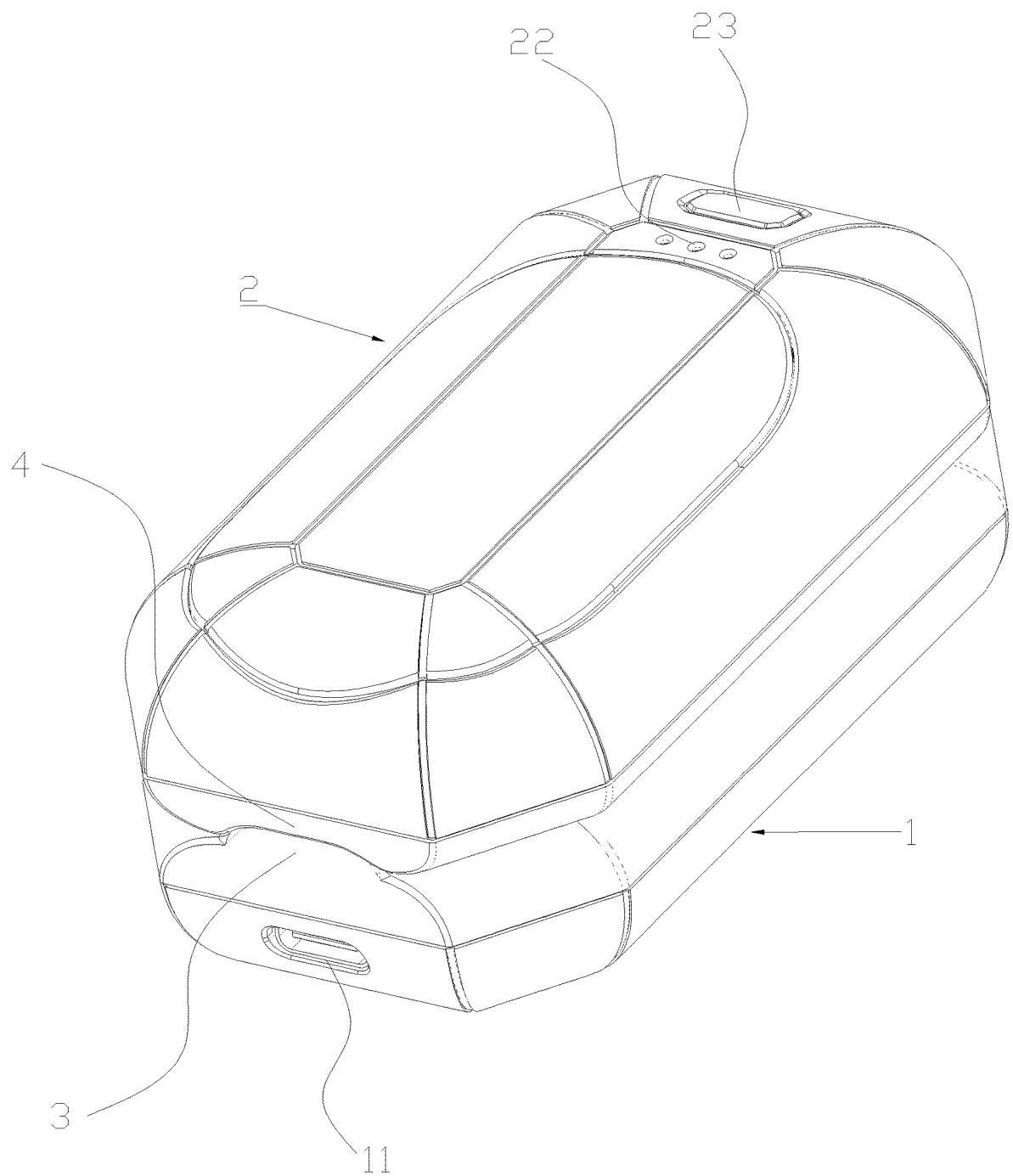

It will be appreciated that for simplicity and clarity of illustration, where appropriate, reference numerals have been repeated among the different figures to indicate corresponding or analogous elements. In addition, numerous specific details are set forth in order to provide a thorough understanding of the exemplary embodiments described herein. However, it will be understood by those of ordinary skill in the art that the exemplary embodiments described herein may be practiced without these specific details. In other instances, methods, procedures, and components have not been described in detail so as not to obscure the related relevant feature being described. Also, the description is not to be considered as limiting the scope of the exemplary embodiments described herein. The drawings are not necessarily to scale and the proportions of certain parts may be exaggerated to better illustrate details and features of the present disclosure.

The term "comprising" when utilized, means "including, but not necessarily limited to"; it specifically indicates open-ended inclusion or membership in the so-described combination, group, series, and the like. The disclosure is illustrated by way of example and not by way of limitation in the figures of the accompanying drawings in which like references indicate similar elements. It should be noted that references to "an" or "one" embodiment in this disclosure are not necessarily to the same embodiment, and such references can mean "at least one". In addition, the terms "first" and "second" are used for descriptive purposes only and cannot be understood as indicating or implying relative importance or implying the number of indicated technical features. Thus, the features defined as "first" and "second" may explicitly or implicitly include one or more of the said features. In the description of embodiments of the application, "a plurality of" means two or more, unless otherwise specifically defined.

Figure 2:
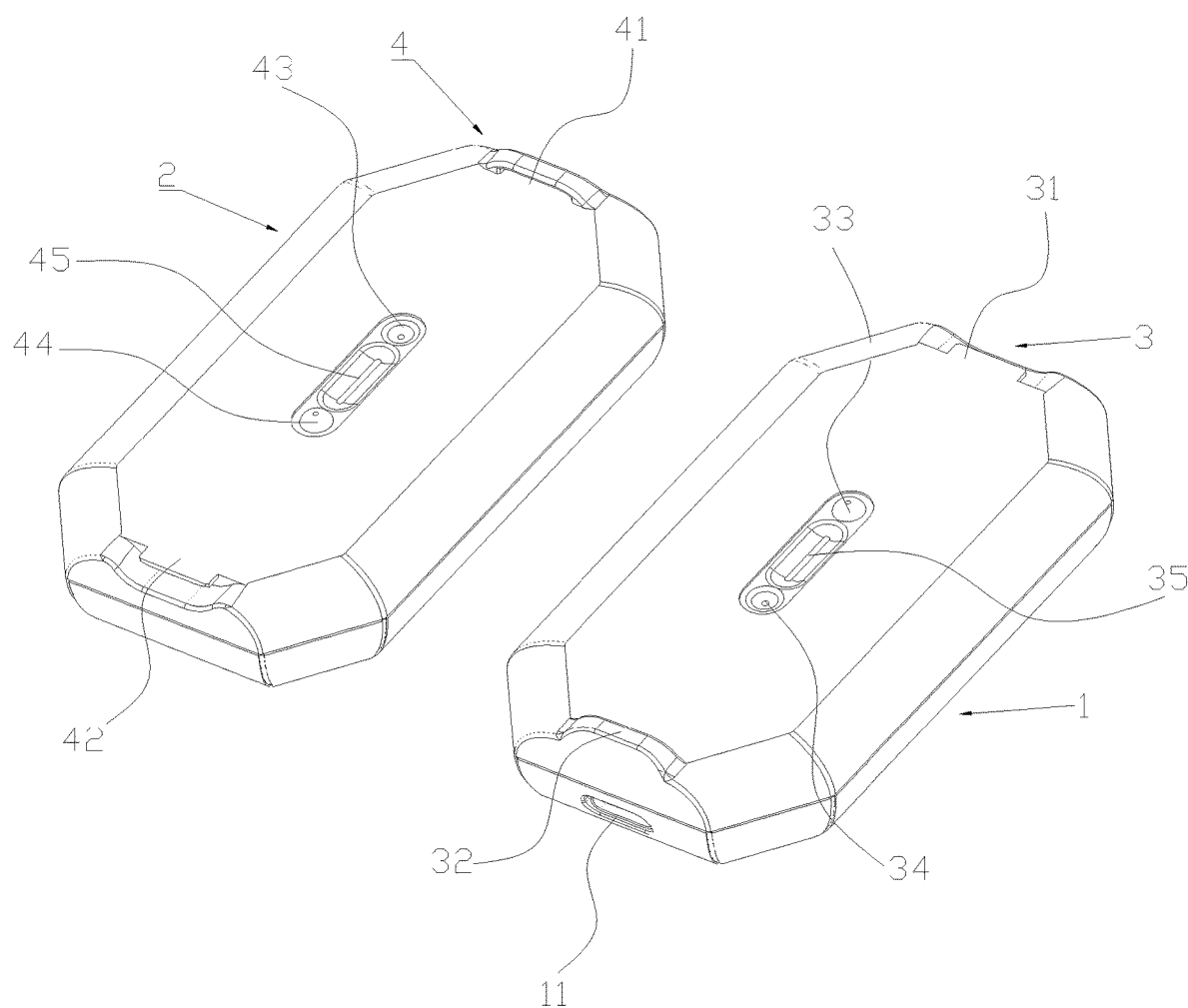
FIG. 2 is an exploded diagram of the present disclosure.
Figure 3:
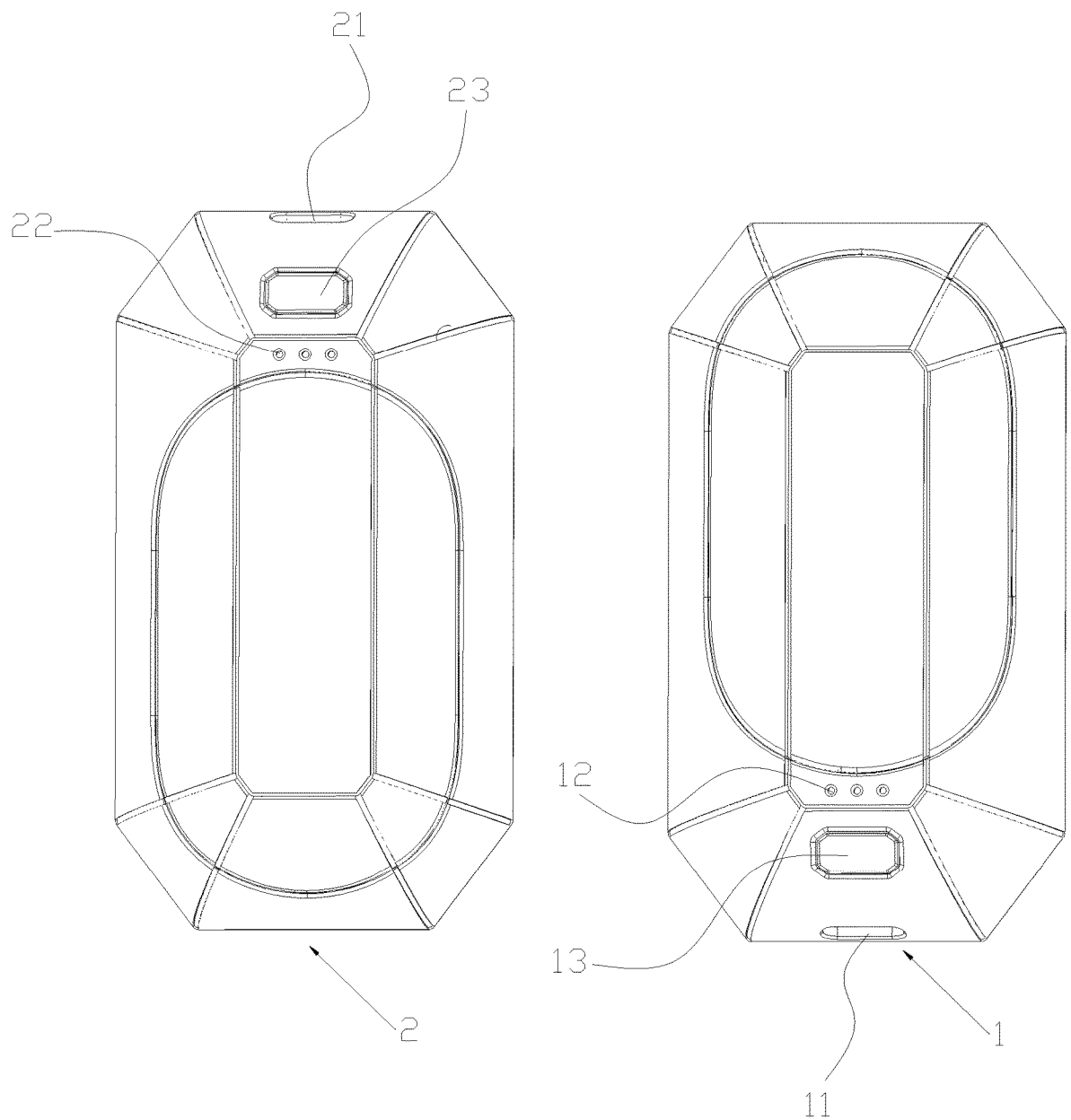
FIG. 3 is another exploded diagram of the present disclosure.
Figure 4:
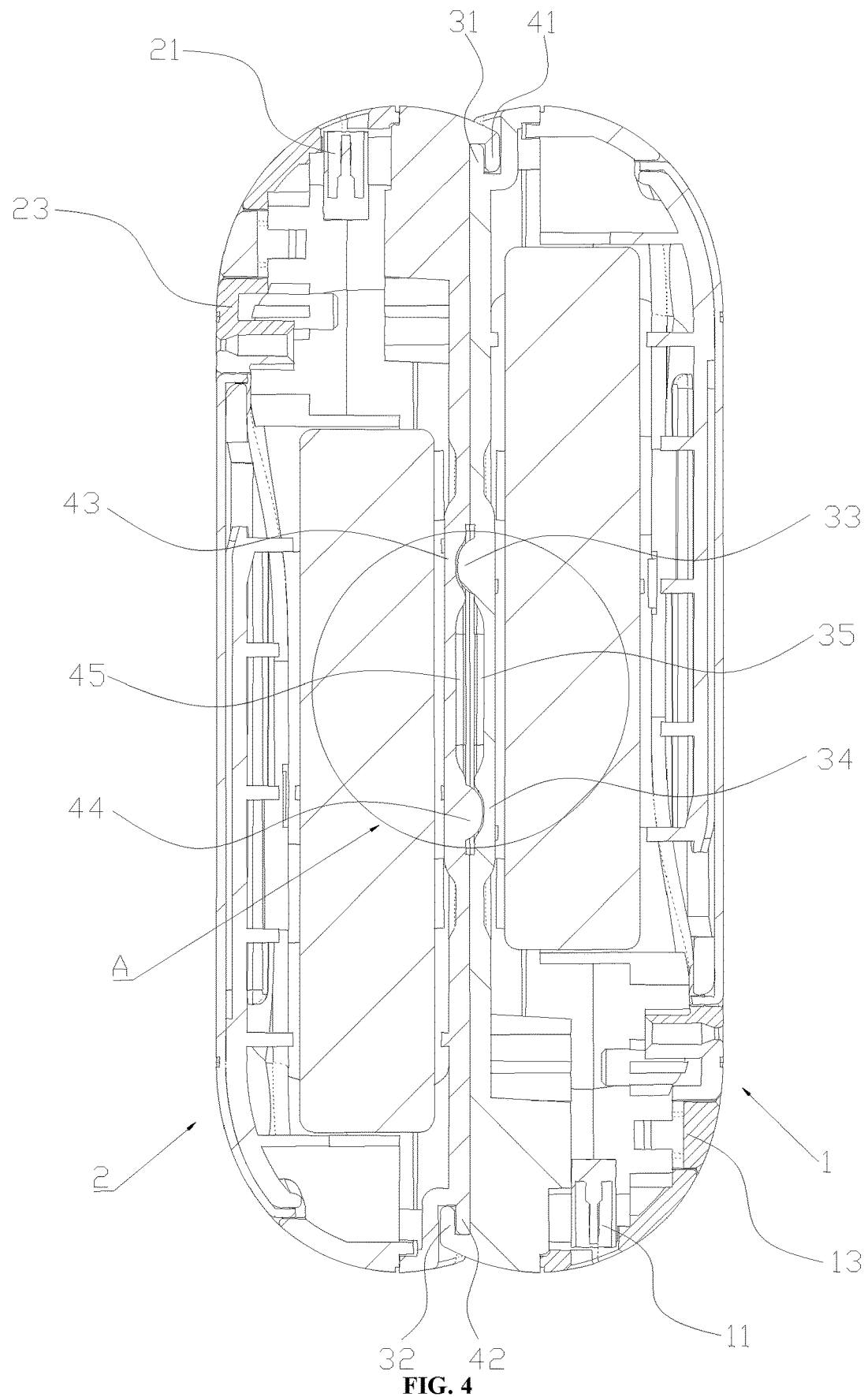
FIG. 4 is a sectional view of sectioning along a first connection part and a second connection part.
Figure 5:
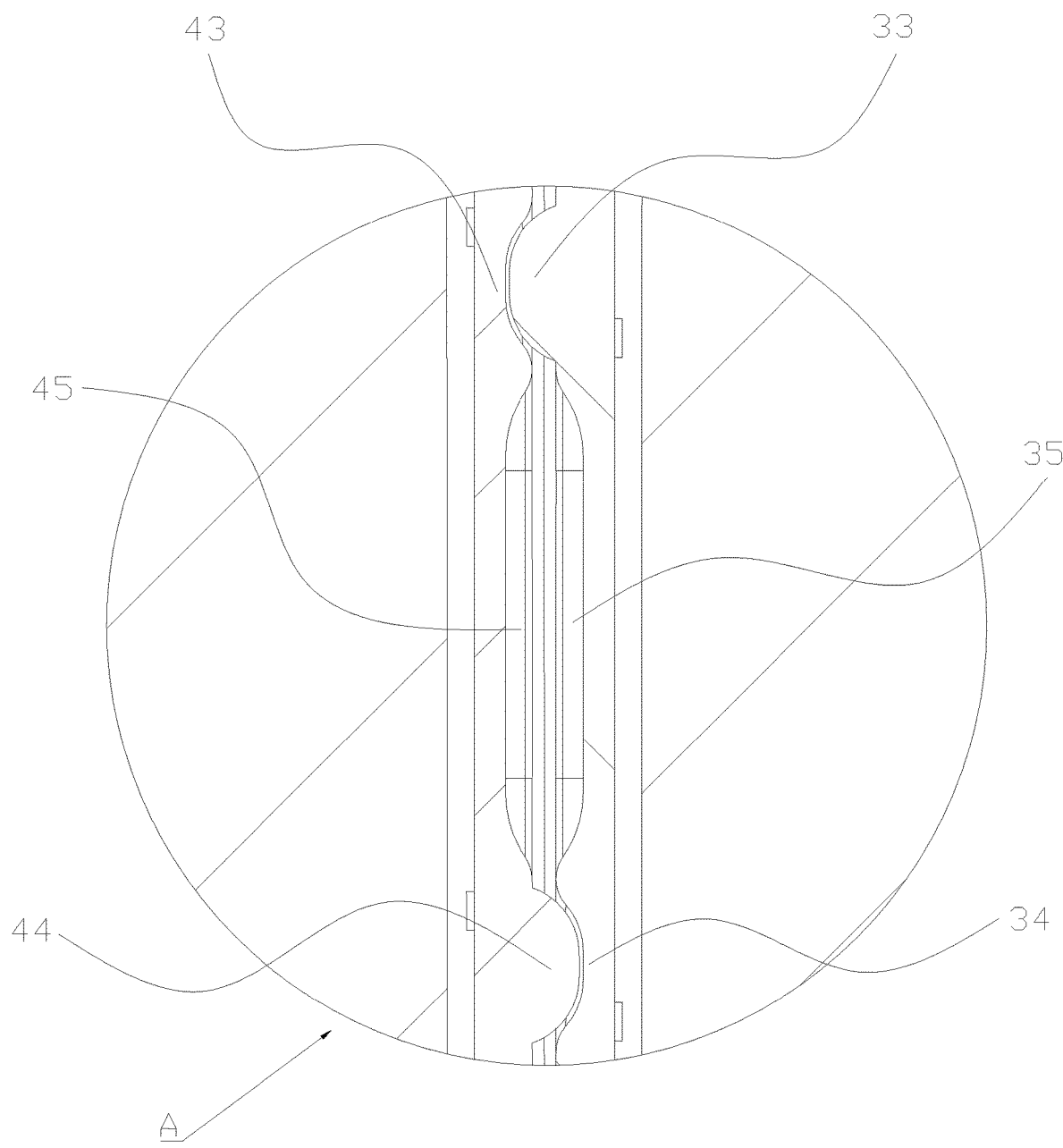
FIG. 5 is an enlarged diagram of the part A of FIG. 4.

Referring to FIG. 1 to FIG. 5, a combined type hand warmer includes a first hand warmer unit 1 and a second hand warmer unit 2; a first connection part 3 is arranged on the first hand warmer unit 1, and a second connection part 4 is arranged on the second hand warmer unit 2; and the first connection part 3 is detachably connected to the second connection part 4 such that the first hand warmer unit 1 and the second hand warmer unit 2 are combined into a whole. By the above structure, the combined type hand warmer includes the first hand warmer unit and the second hand warmer unit; the first connection part is arranged on the first hand warmer unit, and the second connection part is arranged on the second hand warmer unit; and the first connection part is detachably connected to the second connection part such that the first hand warmer unit and the second hand warmer unit are combined into a whole. Therefore, when a user needs to warm two hands/multiple body parts, the first hand warmer unit can be separated from the second hand warmer unit, and the first hand warmer unit and the second hand warmer unit can be respectively used for warming the two hands/multiple body parts. When the user only needs to warm one hand/one body part, the first connection part can be connected to the second connection part to combine the first hand warmer unit with the second hand warmer unit into a whole, so as to enlarge a warming area of the hand warmer for one hand/one body part and enhance the warming effect. Furthermore, when the user needs to carry or store the hand warmer, the user selects, according to an actual situation, either to separately carry or store the first hand warmer and the second hand warmer, or to carry or store the first hand warmer and the second hand warmer as a whole, so as to satisfy a plurality of use scenarios of the user and greatly improve the experience of the user.

The first connection part 3 includes a first buckle 31, and the second connection part 4 includes a first buckle slot 41; and the first buckle 31 is detachably plugged to the first buckle slot 41. The first connection part 3 further includes a second buckle slot 32, and the second connection part 4 further includes a second buckle 42; and when the first buckle 31 is detachably plugged to the first buckle slot 41, the second buckle 42 is detachably plugged to the second buckle slot 32. By the above structure, the structure is simple, and the connection is stable, so that the detachable connection between the first connection part and the second connection part is effectively achieved. Furthermore, in this embodiment, the first connection part and the second connection part can also be detachably connected using male and female fasteners, hook and loop fasteners and the like.

The first connection part 3 further includes a first positioning pillar 33, and the second connection part 4 further includes a first positioning hole 43; and when the first positioning pillar 33 is located in the first positioning hole 43, the first buckle 31 is detachably plugged to the first buckle slot 41, and the second buckle 42 is detachably plugged to the second buckle slot 32. The first connection part 3 further includes a second positioning hole 34, and the second connection part 4 further includes a second positioning pillar 44; and when the first positioning pillar 33 is located in the first positioning hole 43, and the second positioning pillar 44 is located in the second positioning hole 34, the first buckle 31 is detachably plugged to the first buckle slot 41, and the second buckle 42 is detachably plugged to the second buckle slot 32. Specifically, the first connection part 3 further includes a first guide slot 35; the first positioning pillar 33 is located on an upper side of the first guide slot 35, and the second positioning hole 34 is located on a lower side of the first guide slot 35; the second connection part 4 further includes a second guide slot 45; the first positioning hole 43 is located on an upper side of the second guide slot 45, and the second positioning pillar 44 is located on a lower side of the second guide slot 45; and when the first positioning pillar 33 slides into the first positioning hole 43 along the second guide slot 45, and the second positioning pillar 44 slides into the second positioning hole 34 along the first guide slot 35, the first buckle 31 is detachably plugged to the first buckle slot 41, and the second buckle 42 is detachably plugged to the second buckle slot 32. Further, the first buckle 31 is arranged on one side of the first hand warmer unit 1, and the second buckle slot 32 is symmetrically arranged on the other side of the first hand warmer unit 1; and the second buckle 42 is arranged on one side of the second hand warmer unit 2, and the first buckle slot 41 is symmetrically arranged on the other side of the second hand warmer unit 2. By the above structure, it can ensure, by means of the connection between the first positioning pillar and the first positioning hole, and the connection between the second positioning pillar and the second positioning hole, that the first buckle is fully plugged into the first buckle slot, and the second buckle is fully plugged into the second buckle slot, so as to improve the stability of the connection between the first hand warmer unit and the second hand warmer unit. Furthermore, the first guide slot can ensure that the second positioning pillar quickly and accurately slides into the second positioning hole, and the second guide slot can ensure that the first positioning pillar quickly and accurately slides into the first positioning hole, so as to quickly and accurately plug the first buckle into the first buckle slot and plug the second buckle into the second buckle slot to complete connection between the first hand warmer unit and the second hand warmer unit and combine the first hand warmer unit with the second hand warmer unit into a whole. Further, the first positioning pillar is located in the first positioning hole, and the second positioning pillar is located in the second positioning hole, which can effectively prevent the first positioning pillar from sliding out of the first positioning hole and prevent the second positioning pillar from sliding out of the second positioning hole, thus preventing relative sliding between the first hand warmer unit and the second hand warmer unit and preventing the first hand warmer unit from being loosened from the second hand warmer unit. Much further, when the user needs to separate the first hand warmer unit from the second hand warmer unit, the user only needs to slide the first positioning pillar out of the first positioning hole and slide the second positioning pillar out of the second positioning hole, so as to slide the first buckle out of the first buckle slot and slide the second buckle out of the second buckle slot, thus completing the separation of the first hand warmer unit from the second hand warmer unit. It is convenient for the user to use the first hand warmer unit and the second hand warmer unit to warm multiple body parts, and the first hand warmer unit and the second hand warmer unit can even be provided for different people for use; meanwhile, it is also convenient for the user to separately carry and store the first hand warmer unit and the second hand warmer unit, and the user can even carry the first hand warmer unit and the second hand warmer unit separately after putting them in pockets.

A first charging port 11 is further arranged on the first hand warmer unit 1; the first charging port 11 is used for charging the first hand warmer unit 1; a second charging port 21 is further arranged on the second hand warmer unit 2; and the second charging port 21 is used for charging the second hand warmer unit 2. A first power indicator 12 is further arranged on the first hand warmer unit 1; the first power indicator 12 is used for displaying the battery power of the first hand warmer unit 1; a second power indicator 22 is further arranged on the second hand warmer unit 2; and the second power indicator 22 is used for displaying the battery power of the second hand warmer unit 2. Specifically, a first on/off button 13 is further arranged on the first hand warmer unit 1; the first on/off button 13 is used for controlling the first hand warmer unit 1 to be turned on/off; a second on/off button 23 is further arranged on the second hand warmer unit 2; and the second on/off button 23 is used for controlling the second hand warmer unit 2 to be turned on/off. By the above structure, the user can charge the first hand warmer unit through the first charging port and charge the second hand warmer unit through the second charging port, and can observe the residual battery power of the first hand warmer unit through the first power indicator and observe the residual battery power of the second hand warmer unit through the second power indicator. Further, the user can further select to power on or off the first hand warmer unit through the first on/off button and select to power on or off the second hand warmer unit through the second on/off button.

The above description only describes embodiments of the present disclosure, and is not intended to limit the present disclosure, various modifications and changes can be made to the present disclosure. Any modifications, equivalent substitutions, improvements, etc. made within the spirit and scope of the present disclosure are intended to be included within the scope of the present disclosure.

What is claimed is:

1. A combined type hand warmer, comprising a first hand warmer unit and a second hand warmer unit; a first connection part is arranged on the first hand warmer unit, and a second connection part is arranged on the second hand warmer unit; and the first connection part is detachably connected to the second connection part such that the first hand warmer unit and the second hand warmer unit are combined into a whole,
    wherein the first connection part comprises a first buckle, and the second connection part comprises a first buckle slot; and the first buckle is detachably plugged to the first buckle slot,
    wherein the first connection part further comprises a second buckle slot, and the second connection part further comprises a second buckle; and when the first buckle is detachably plugged to the first buckle slot, the second buckle is detachably plugged to the second buckle slot.

2. The combined type hand warmer according to claim 1, wherein the first connection part further comprises a first positioning pillar, and the second connection part further comprises a first positioning hole; and when the first positioning pillar is located in the first positioning hole, the first buckle is detachably plugged to the first buckle slot, and the second buckle is detachably plugged to the second buckle slot.

3. The combined type hand warmer according to claim 2, wherein the first connection part further comprises a second positioning hole, and the second connection part further comprises a second positioning pillar; and when the first positioning pillar is located in the first positioning hole, and the second positioning pillar is located in the second positioning hole, the first buckle is detachably plugged to the first buckle slot, and the second buckle is detachably plugged to the second buckle slot.

4. The combined type hand warmer according to claim 3, wherein the first connection part further comprises a first guide slot; the first positioning pillar is located on an upper side of the first guide slot, and the second positioning hole is located on a lower side of the first guide slot; the second connection part further comprises a second guide slot; the first positioning hole is located on an upper side of the second guide slot, and the second positioning pillar is located on a lower side of the second guide slot; and when the first positioning pillar slides into the first positioning hole along the second guide slot, and the second positioning pillar slides into the second positioning hole along the first guide slot, the first buckle is detachably plugged to the first buckle slot, and the second buckle is detachably plugged to the second buckle slot.

5. The combined type hand warmer according to claim 2, wherein the first buckle is arranged on one side of the first hand warmer unit, and the second buckle slot is symmetrically arranged on the other side of the first hand warmer unit; and the second buckle is arranged on one side of the second hand warmer unit, and the first buckle slot is symmetrically arranged on the other side of the second hand warmer unit.

6. The combined type hand warmer according to claim 1, wherein a first charging port is further arranged on the first hand warmer unit; the first charging port is used for charging the first hand warmer unit; a second charging port is further arranged on the second hand warmer unit; and the second charging port is used for charging the second hand warmer unit.

7. The combined type hand warmer according to claim 6, wherein a first power indicator is further arranged on the first hand warmer unit; the first power indicator is used for displaying the battery power of the first hand warmer unit; a second power indicator is further arranged on the second hand warmer unit; and the second power indicator is used for displaying the battery power of the second hand warmer unit.

8. The combined type hand warmer according to claim 7, wherein a first on/off button is further arranged on the first hand warmer unit; the first on/off button is used for controlling the first hand warmer unit to be turned on/off; a second on/off button is further arranged on the second hand warmer unit; and the second on/off button is used for controlling the second hand warmer unit to be turned on/off.

\* \* \* \* \*